United States Patent [19]

Somers

[11] Patent Number: 4,556,663
[45] Date of Patent: Dec. 3, 1985

[54] BENZOYLECGONINE, BENZOYLNORECGONINE AND ECGONINE AS ACTIVE AGENTS FOR THE TREATMENT OF RHEUMATOID ARTHRITIS AND OSTEOARTHRITIS

[76] Inventor: Lowell M. Somers, 46861 Madison, Indio, Calif. 92201

[21] Appl. No.: 646,586

[22] Filed: Aug. 31, 1984

Related U.S. Application Data

[63] Continuation-in-part of Ser. No. 448,928, Dec. 13, 1982, Pat. No. 4,469,700, which is a continuation of Ser. No. 275,307, Jun. 19, 1981, abandoned.

[51] Int. Cl.$^4$ ............................................. A01K 31/44
[52] U.S. Cl. .................................................... 514/304
[58] Field of Search .......................................... 424/265

[56] References Cited
PUBLICATIONS

Misra et al., Research Comm. in Chemical Pathology & Pharmacology, vol. 8, pp. 55–63 (1974).
Bell and Archer, J.A.C.S., vol. 82, pp. 4642–4644 (1960).
J. Pharm. Pharmac., 1969, 21, Supp., "Excretion of Cocaine and its Metabolites in Man", by F. Fish, et al., pp. 135S–138S.
Radioaktive Markierung von Tropan-Alkaloiden, II (German), 1962, "Synthetischer Einbau von 14C in (−)-Cocain, etc.", by H. L. Schmidt, et al., pp. 184–194.
Research Communications in Chem. Path. & Pharm., vol. 11, No. 4, Aug. 1975, pp. 663–666.
Medical World News, Oct. 15, 1979, pp. 19–20, "FP Giving Cocaine for Arthritis is Beset but Gains a Major Ally."
Arthritis News Today, vol. 2, No. 7, Apr. 1980 "Esterene in the Treatment of Rheumatoid Arthritis," (8 pages).
Communications, J. Pharm. Pharmac., 1975, 27, 784–786, "Estimation and Disposition of ($^3$H) benzoylecgonine and Pharmacological Activity of Some Cocaine Metabolites."
Life Sciences, vol. 19, pp. 1585–1596, 1976, "Intracellular Disposition of ($^3$H)-Cocaine, etc.", by Salvatore J. Mule, et al.
Abstract, CA 83, 172 831b "Calcium–B . . . , (1975).
Research Communications in Chemical Patho. Pharm., "Disposition of ($^3$H) Benzoylnorecgonine (Cocaine Metabolite) in the Rat", by A. L. Misra, et al., vol. 13, No. 4, Apr. 1976, pp. 579–584.

Primary Examiner—Stanley J. Friedman
Attorney, Agent, or Firm—Klein & Szekeres

[57] ABSTRACT

Pharmaceutical preparations containing benzoylecgonine, benzoylnorecgonine, and ecgonine are disclosed for treatment of rheumatoid arthritis, and in case of benzoylecgonine and benzoylnorecgonine for the treatment of osteoarthritis as well. The pharmaceutical preparations containing the active compounds are administered to human patients in effective amounts orally, through inhalation, transdermally or through the mucosal membranes.

15 Claims, No Drawings

BENZOYLECGONINE, BENZOYLNORECGONINE AND ECGONINE AS ACTIVE AGENTS FOR THE TREATMENT OF RHEUMATOID ARTHRITIS AND OSTEOARTHRITIS

CROSS REFERENCE TO RELATED APPLICATIONS

This application is a continuation-in-part of presently pending application Ser. No. 448,928, filed on Dec. 13, 1982, which is a continuation of application Ser. No. 275,307, filed on June 19, 1981, now abandoned. Application Ser. No. 448,928 was issued as U.S. Pat. No. 4,469,700 on Sept. 4, 1984.

BACKGROUND OF THE INVENTION

1. Field of the Invention

This invention relates to pharmaceutical compositions, dosage forms and their use in the treatment of chronic disease. More particularly, it concerns pharmaceutical compositions and dosage forms and their use in the treatment of the pain and locomotor dysfunction of rheumatoid arthritis, and osteoarthritis.

2. Discussion of Prior Art

Rheumatoid arthritis is a serious, often crippling, disease characterized by pain and locomotor dysfunction. As pointed out by Nickander et al in their article "Nonsteroidal Antiinflammatory Agents" which appeared at *Ann. Rev. Pharmacol. Toxicol.*, 1979, 19:469-90, this sort of pain and locomotor dysfunction are among man's most common and frustrating afflictions. The gravity of this disease has led to the investigation and/or adoption of a wide range of drugs for its alleviation. Aspirin has been commonly used since the turn of this century. Other major drugs for arthritis have historically included indomethacin, other salicylates, phenylbutazone, steroids and gold. While more recently, fenoprofen, ibuprofen, naproxen, sulindac and tolmetin have been approved for use in the United States.

While these compounds can offer antiinflammatory, antipyretic and analgesic effects and have proven helpful in the management of rheumatoid arthritis in many patients, when combined with other modalities such as proper rest, exercise, physical therapy and surgery, they are less than ideal. Many exhibit serious side effects with many patients, particularly gastrointestinal damage and renal toxicity. Each of these materials have the failing of being far from universal—some patients will respond to one material while others respond favorably only to others.

Osteoarthritis is classified as a degenerative joint disease (Cecil-Loeb TEXTBOOK OF MEDICINE, 13th Edition, W. B. Saunders Co., Beeson and McDermott Editors). This painful disease is similar in many respects to rheumatoid arthritis in its symptoms and effects on the patient's well being. Salicylates, such as aspirin, phenylbutazone, and other analgesics and antiflammatory agents, have been used in the prior art to alleviate the symptoms of osteoarthritis.

Cocaine and cocaine free base have been employed in the management of rheumatoid arthritis for a number of years. I have demonstrated, through clinical experiments on a range of patients suffering from rheumatoid arthritis, the effectiveness of this treatment.

Unfortunately for this possible therapeutic use, cocaine and cocaine free base are widely regarded as materials of abuse. It is most unlikely that the regulatory and drug enforcement agency issues will ever be resolved to a point that cocaine or its free base can be available on as widespread a basis as would be required for their use in the treatment of sufferers of rheumatoid arthritis. In addition, certain individuals can develop dependence upon these materials and/or exhibit symptoms of intoxication when using them.

The metabolic pathway for the degradation of the alkaloid cocaine in experimental animals and man has been extensively studied. Moreover, numerous synthetic analogs and derivatives of the alkaloid have been made. The following articles, publications and patents are examples of the vast scientific literature related to cocaine, its metabolites and derivatives: Disposition of [$^3$H] benzoylnorecgonine (Cocaine Metabolite) in the Rat, by A. L. Misra, et al., Research Communications in Chemical Pathology and Pharmacology, Volume 13, pages 579-584 (1976); Physiologic Distribution and Metobolism of [$^3$H] Ecgonine (Cocaine Metobolite) in the Rat, by A. L. Misra, et al., Research Communications in Chemical Pathology and Pharmacology, Volume 8, pages 55-63 (1974); Excretion of Cocaine and its Metobolites in Man, by F. Fish, et al., J. Pharm. Pharmac., 21 *Suppl.*, 135S-138S (1969); U.S. Pat. Nos. 2,948,730 and 2,893,966.

In addition to the investigative studies which shed light on the metabolic fate of the therapeutically effective but dangerous substance cocaine, what is needed even more in the healing arts is effective treatment of rheumatoid arthritis and osteoarthritis by derivatives of cocaine which, however, have no significant potential for abuse. More specifically, what is needed is a pharmaceutical preparation and/or dosage form and a method for its use that does not involve cocaine or its free base, that does not present the untoward physiological effects of cocaine but which acts therapeutically in the manner of cocaine to alleviate the pain and motor dysfunction of rheumatoid arthritis and of osteoarthritis.

STATEMENT OF THE INVENTION

It has now been found that benzoylecgonine, benzoylnorecgonine, and levorotatory ecgonine are therapeutically effective for alleviation of the pain of rheumatoid arthritis and restoration of motor dysfunction of rheumatoid arthritis in humans and other mammals. The compounds are preferably administered in carriers as pharmaceutically acceptable formulations. Moreover, benzoylecgonine and benzoylnorecgonine are therapeutically effective for alleviation of the pain and symptoms of osteroarthritis.

DETAILED DESCRIPTION OF THE INVENTION

Benzoylecgonine (Compound I), benzoylnorecgonine (Compound II), and ecgonine (Compound III) are the active agents employed herein for the treatment of rheumatoid arthritis (Compound I), and benzoylecgonine and benzoylnorecgonine for the treatment of osteoarthritis.

Fish and Wilson, in *J. Pharm. Pharmac.*, 1969 21 Suppl., 135S-138S, presented results showing formation of benzoylecgonine

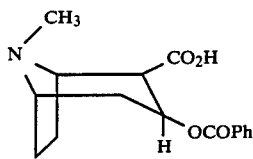

Compound I by mammals as a metabolite of cocaine. Misra, et al. summarized and reported at Volume 13, No. 4, *Research Communications in Chemical Pathology and Pharmacology* (April, 1976, page 579), the finding of benzoylnorecgonine,

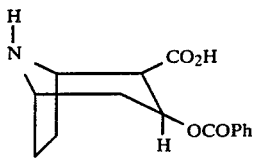

Compound II

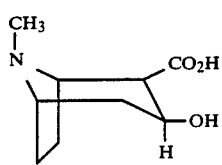

Compound III as a mammalian cocaine metabolite, as well. Ecgonine is described as a metobolite of cocaine, for example, in a publication of A. L. Misra, et al., Research Communications in Chemical Pathology and Pharmacology, Volume 8, pages 55–63 (1974), which is cited in the introductory section of the present application for patent.

Routes for the synthesis of Compounds I-III have been published. Schmidt and Werner disclose in *Ann.* 653, 184–194 (1962) the conversion of benzoylecgonine (I) to benzoylnorecgonine (II) by, for example, putting 1.16 g of I in 250 cc $H_2O$, adding, over 30 minutes, 48 cc of 3% $KMnO_4$ and stirring for 5 hours at a pH held below 8 by gradual $H_2SO_4$ addition and thereafter filtering and recovering (II) by freeze drying and repeated recrystallization from ethanol. Findlay in *J. Amer. Chem. Soc.* 82 (1960), pages 4642–4644, discloses that benzoylecgonine can be formed by refluxing cocaine in water for 10 hours and then cooling to recover the benzoylecgonine by crystallization. The preparation of ecgonine is described in German Pat. No. 47,602, and by Bell and Archer, in *Journal of the American Chemical Society*, Volume 82, pages 4642–4644 (1960). Reference to ecgonine is made in U.S. Pat. Nos. 2,948,730 and 2,893,996.

Method of Administration

Administration of a therapeutically effective dose of the active compounds (Compounds I through III) to a human or other warm blooded patient afflicted with rheumatoid arthritis or osteoarthritis can be via appropriate pharmaceutical formulation and any of the accepted modes for repeated administration of agents for the treatment of inflamation or pain and the prophylaxis thereof. Thus, administration can be, for example, orally, rectally, locally, nasally, vaginally, topically (for transdermal delivery), or via inhalation. The formulations suitable for such modes of administration include solid, semisolid, and liquid formulations which can include tablets, pills, capsules, powders, solutions, suspensions, creams, lotions, ointments, or the like, preferably in unit dosage forms suitable for simple administration of precise dosages.

Oral administration of benzoylecgonine or norbenzoylecgonine (Compound I and II) for the treatment of rheumatoid arthritis is effected using a convenient daily dosage regimen, such as from 3 to 8 doses per day, preferably 4–6 doses per day, which can be adjusted according to the degree of affliction. Generally, a daily dose of from 1.5 to about 15 mg of the active benzoylecgonine and/or benzoylnorecgonine per kilogram of body weight is used. Most conditions respond to treatment comprising a dosage level of the order of 2.5 to 10 mg per kilogram of body weight per day.

For the treatment of osteoarthritis with Compounds I and/or II, the oral administration is similar in terms of daily dose regimens and quantities of administered compounds, as given above for the treatment of rheumatoid arthritis with the same compounds (benzoylecgonine and benzoylnorecgonine). Thus, 3–8 oral doses per day, preferably 4–6 doses per day, are used. The total daily oral dose is from about 1.5 to about 15 mg of Compound I or II per kilogram body weight of the patient.

For the treatment of rheumatoid arthritis with ecgonine (Compound III) the daily oral dose regimen, and dosage per body weight of patient, is approximately the same as given above. This means individual oral doses of approximately 0.187 mg to about approximately 5.0 mg of Compounds I, II, or III for the treatment of rheumatoid arthritis, and of Compounds I and II for osteoarthritis, per kg body weight.

In the above-described oral modes of administration, a pharmaceutically acceptable nontoxic composition is formed by the incorporation of any of the normally employed excipients, such as, for example, pharmaceutical grades of mannitol, lactose, starch, magnesium stearate, talcum, cellulose, glucose, gelatin, sucrose, magnesium carbonate, and the like. Of course, if desired, other pharmacologically active materials can be incorporated into such formulations to give a combination product.

Transdermal delivery of the benzoylecgonine, benzoylnorecgonine, and ecgonine compounds, effected by topical administration of a solution, suspension, cream, lotion, or similar formulation to the skin of the patient is also effective. More specifically, transdermal delivery of Compounds I, II, and III is effective for treatment of rheumatoid arthritis, and of Compounds I and II for osteoarthritis. Formulations for such use include a carrier which should be a liquid or semisolid that is inert to the active compound and not irritating to the skin. Suitable carriers for solutions include water, aqueous mixed solvents, lower alkanols and alkandiols, for example, ethanol, methanol, isopropanol, ethylene glycol, glycerine, propylene glycol, and the like. Suitable bases for salves and creams include pharmaceutically acceptable oils and cream bases and gells. In addition, topical formulations can contain nontoxic auxilary substances, such as wetting or emulsifying agents, pH buffering agents, and the like. In general, it is preferred to use formualtions in which the active compounds are soluble, preferably at least to an extent of about 1% by weight. Propylene glycol is a particularly preferred vehicle for the transdermal administration of Compounds I, II, and III.

In the transdermal (topical) mode of administration, typically from 50 to 500, preferably 300, square centimeters of skin surface is contacted with a 1 to 10% by weight solution or cream of the active compound at least once a day, and preferably from three to eight times per day, and still more preferably four to six times per day, the exact dosage depending upon the degree of affliction. The formulations employed in the transdermal mode of application can, if desired, contain materials to promote transdermal transport. The aforesaid alkanols and alkandiols, for example, may promote such transport as may DMSO, surfactants, and the like. In addition, other materials may be added to minimize skin irritation or to treat other conditions or side reactions.

Ecgonine (Compound III) is preferably administered transdermally for the treatment of rheumatoid arthritis in a propylene glycol vehicle, as a 1 to 10%, preferably 5% by weight solution for the active compound, in a total daily dose range of approximately 10 mg to approximately 300 mg, a maximum single dose being approximately 100 mg and a minimum single dose being approximately 5 mg.

Benzoylecgonine and benzoylnorecgonine (Compounds I and II) are preferably administered transdermally for the treatment of osteoarthritis in a propylene glycol vehicle as a 1 to 10%, preferably 5%, by weight solution for the active compounds, in a total daily dose range of approximately 10 to 200 mg, preferably in a single daily dose of approximately 100 mg of the active compound.

A third mode of administration of the Compounds I, II, and III for rheumatoid athritis and Compounds I and II for osteoarthritis that is useful, is via the mucous membranes of the oral and nasal cavities. This method of administration can be effected using buccal patches or the like for sublingual administration or by inhaling the active compounds as a finely divided powder or atomized solution. With inhalation therapy, the compounds can be delivered to the nasal membranes and to the lungs as a solid powder or as a solution. In either method, the patient can supply the driving force by inhaling or an external force can be used such as a pump, a propellant gas or liquid, or the like. In this mode of therapy, a daily dosage regimen of at least one dose per day is followed, with three to eight doses per day being preferred. Generally, the amount of active compound delivered per day is at least 0.5 mg per kilogram of body weight. Preferably, the amount of active compound administered per day by inhalation is from 1 to about 8 mg per kilogram of body weight.

In addition, the benzoylecgonine, benzoylnorecgonine, or ecgonine active compounds (Compounds I, II, and III) can be administered via vaginal or uteral routes wherein the active compound in a suitable liquid or ointment carrier is applied to the vaginal or uteral membranes. This method of administration employs similar dosages and dosage regimens described above for buccal or nasal administration.

The invention will be further illustrated by the following EXAMPLES. These are presented to exemplify and make clear the invention and are not to be construed as limiting its scope which is defined solely by the claims.

EXAMPLE 1

A. Benzoylecgonine and benzoylnorecgonine are prepared from commercial cocaine by the above-described methods of Finlay and Schmidt and Werner, respectively. The two active compounds are formulated with sorbitol as a powder containing 50% active agent, in sterile water as a 4% solution, and in a carboxymethylcellulose jelly at a 2% concentration.

The active compounds could also, if desired, be presented in association with other pharmaceutically acceptable carriers in pharmaceutical formulations suitable for transdermal, inhalation, nasal, oral, or rectal administration. Suitable carriers include solids such as lactose, starch (pharmaceutical grade), dicalcium phosphate, calcium sulfate, kaolin, mannitol, and powdered sugar, and liquids such as sterile saline or the like.

The formulations for oral, rectal, or vaginal administration are advantageously presented in discrete unit dosage forms, such as tablets, capsules, cachets, suppositories, each containing a predetermined amount of the compound, but may also be presented as a powder, or as granules. They may, as well, be presented as a solution or suspension in an aqueous or nonaqueous liquid, such as would be useful for administration. The formulations may be made by any of the known methods and may include one or more of the following accessory ingredients: buffers, flavoring, binding, dispersing, surface-active, thickening, lubricating, and coating materials, preservatives, bacteriostats, antioxidants, suppository and ointment bases, coloring agents, and any other acceptable excipients. Unit dosage forms may typically contain from about 0.01 to about 0.1 gram of active compound.

Any skilled artisan can prepare these dosage forms by simply referring to the oral dosage form preparatory procedure outline in "Remington's Pharmaceutical Sciences", 14th Edition (1970), pages 1624–1698, inclusive, and the rectal dosage form preparatory procedure outline in the same text at pages 1617–1624, inclusive.

B. A group of patients afflicted with rheumatoid arthritis is assembled. They are in pain and have pronounced motor dysfunction as results of their disease. A control group is taken from this group and left untreated. The members of the control group show no improvement during the test. A first test group is selected at random from the patient group. Each member of this first test group rubs 2–4 g quantities of the jelly (40–80 mg of the active compound) on their skin three times a day. A second test group takes, by inhalation, 100 mg doses of the powder six times a day. A third test group rubs 1–2 ml quantities of the 4% solution on their skin and allows it to evaporate to dryness. This is carried out six times a day. A fourth test group takes orally six times a day capsules made to contain up to 80 mg of the active compound. The patients in each of the four test groups report a reduction of their pain and an improvement in mobility and motor function during the period that the treatment is being administered to them. They report no adverse effects of their treatment.

EXAMPLE 2

The active compounds are individually formulated into 5% by weight ointments in a water-miscible ointment vehicle consisting of polyethylene glycols and propylene glycol.

When 1 g of either of these ointments is rubbed into the skin of test patients suffering from rheumatoid arthritis in a treatment program of six doses per day or 300 mg of active compound per day, the patients report improvement in mobility and a decrease in the pain that they normally associate with their arthritic condition.

A series of buccal patches is prepared, each incorporating 0.5 g of this ointment. When four to six of these patches are serially placed on the mucous membrane under the tongue, they administer the compound throughout the day. Test subjects afflicted with rheumatoid arthritis report a decrease in pain and an increase in mobility when they are receiving this treatment.

EXAMPLE 3

The active Compounds I and II (benzoylecgonine and benzoylnorecgonine) are formulated into 5% by weight ointments as described in Example 2. A total daily dosage of approximately 200 mg of the active compounds is given transdermally in four equal doses of approximately 50 mg through approximately 300 square centimeters of the skin of patients suffering from osteoarthritis.

After a few days of treatment, all signs of inflamation disappear, swelling of the joints is reduced, pain is alleviated, and range of motion returns to normal.

EXAMPLE 4

The active compound ecgonine (Compound III) is formulated into 5% by weight ointments as described for Compounds I and II in Example 2. A total daily dosage of approximately 150 mg per day of the active compound is given transdermally in 2-8 divided doses to patients suffering from rheumatoid arthritis.

After a few days of treatment, the patients are in complete remission, although in about 50% of the patients, the rheumatoid arthritis reappears 4 days to 1 year after cessation of the drug.

What is claimed is:

1. A pharmaceutical formulation for the treatment of rheumatoid arthritis comprising ecgonine in amounts effective for the treatment of rheumatoid arthritis in human patients afflicted with the disease and a pharmaceutical carrier for said ecgonine said formulation being adapted for administration to patients through inhalation or through mucosal membranes of the patient's body, the formulation being further adapted for administering daily dosages of approximately 1 to 8 miligrams of ecgonine per kilogram body weight of the patient.

2. A pharmaceutical formulation for the treatment of rheumatoid arthritis comprising ecgonine in amounts effective for the treatment of rheumatoid arthritis in human patients afflicted with the disease and a pharmaceutical carrier for said ecgonine, the formulation comprising a water miscible ointment containing a water miscible pharmaceutically acceptable polyol.

3. The formulation of claim 2 wherein the polyol is propylene glycol.

4. The formulation of claim 2 wherein the ointment comprises approximately 1 to 10% by weight of ecgonine.

5. A method for treating rheumatoid arthritis which comprises the oral administration to a human or other warm blooded animal in need of such treatment, an effective amount of ecgonine contained in a pharmaceutical carrier, the method comprising administration of individual oral doses of approximately 0.187 to approximately 5.0 mg of ecgonine to the patient, per kg body weight of the patient.

6. A method for treating rheumatoid arthritis which comprises the administration to a human or other warm blooded animal in need of such treatment, an effective amount of ecgonine contained in a pharmaceutical carrier, the method comprising administration of the ecgonine through inhalation or mucosal membranes of the patient, the pharmaceutical carrier being adapted for such administration.

7. The method of claim 6 wherein the dosages of ecgonine administered daily to the patient are approximately 1 to 8 milligram of ecgonine per kilogram body weight of the patient.

8. A method for treating rheumatoid arthritis which comprises the administration to a human or other warm blooded animal in need of such treatment, an effective amount of ecgonine contained in a pharmaceutical carrier, the method comprising transdermal administration of the ecgonine to the patient, the pharmaceutical carrier being adapted for such transdermal administration.

9. The method of claim 8 wherein the pharmaceutical carrier is a water miscible ointment comprising a pharmaceutically acceptable polyol.

10. The method of claim 9 wherein the polyol is propylene glycol.

11. A method for treating osteoarthritis which comprises the oral administration to a human or other warm blooded animal in need of such treatment, an effective amount of one or more active agent selected from a group consisting of bezoylecgonine and benzoylnorecgonine, contained in a pharmaceutical carrier, the method comprising administration of 3 to 8 oral doses per day to provide, on a per day basis, approximately 1.5 to 15 mg of active agent per kilogram body weight of the patient.

12. A method for treating osteoarthritis which comprises the administration to a human or other warm blooded animal in need of such treatment, an effective amount of one or more active agent selected from a group consisting of bezoylecgonine and benzoylnorecgonine, contained in a pharmaceutical carrier, the method comprising administration of the active compounds to the patient through inhalation or through the mucosal membranes of the patient, the pharmaceutical carrier being adapted for such administration.

13. A method for treating osteoarthritis which comprises the administration to a human or other warm blooded animal in need of such treatment, an effective amount of one or more active agent selected from a group consisting of bezoylecgonine and benzoylnorecgonine, contained in a pharmaceutical carrier, the method comprising transdermal administration of the active compounds to the patient, the pharmaceutical carrier being adapted for such transdermal administration.

14. The method of claim 13 wherein the pharmaceutical carrier is a water miscible ointment comprising a pharmaceutically acceptable polyol.

15. The method of claim 14 wherein the polyol is propylene glycol.

* * * * *